US006353028B2

(12) United States Patent
Easterling

(10) Patent No.: US 6,353,028 B2
(45) **Date of Patent: *Mar. 5, 2002**

(54) COMPOSITION AND METHOD FOR TOPICALLY TREATING PEYRONIE'S DISEASE, DUPUYTREN'S HAND CONTRACTURE, LEDDERHOSE FIBROSIS, ERECTILE DYSFUNCTION ARISING FROM PLAQUE ACCUMULATIONS, AND SCARRING

(76) Inventor: W. Jerry Easterling, c/o Prescription Dispensing Laboratories, Inc., 8400 Blanco Rd., San Antonio, TX (US) 78216

( * ) Notice: Subject to any disclaimer, the term of this patent is extended or adjusted under 35 U.S.C. 154(b) by 0 days.

This patent is subject to a terminal disclaimer.

(21) Appl. No.: 09/411,175

(22) Filed: Oct. 1, 1999

Related U.S. Application Data

(63) Continuation-in-part of application No. 09/128,103, filed on Aug. 3, 1998, now Pat. No. 6,031,005.

(51) Int. Cl.[7] .............................................. A61K 31/135

(52) U.S. Cl. ....................... 514/654; 514/937; 514/944; 424/78.02

(58) Field of Search ................................ 514/654, 944, 514/937; 424/78.02

(56) References Cited

U.S. PATENT DOCUMENTS

| | | | |
|---|---|---|---|
| 4,338,300 A | | 7/1982 | Gelbard |
| 5,139,944 A | | 8/1992 | Sawyer |
| 5,242,391 A | | 9/1993 | Place |
| 5,474,535 A | | 12/1995 | Place |
| 5,569,678 A | | 10/1996 | Lee |
| 5,731,339 A | | 3/1998 | Lowrey |
| 5,773,020 A | | 6/1998 | Place |
| 5,902,609 A | | 5/1999 | Lee |
| 6,113,939 A | * | 9/2000 | Place et al. |

OTHER PUBLICATIONS

Pirozzi–Farina et al. "Ultrasonographic Findings in the Medical Treatment of I.P.P.: Our Indications"; Acta Urologica Italica; vol. 11, No. 6, 459–461; 1997.*

Levine, et al Intralesional Verapamil Injection for the Treatment of Peyronie's Disease:, Journal of Urology; vol. 151, 1522–1524; 1994.

Levine, "Treatment of Peyronie's Disease with Intralesional Verapamil Injection"; Journal of Urology; vol. 158, 1395–1399; 1997.

Jamil, et al; "Use of Intralesional Verapamil to Dissolve Peyronie's Disease Plaque: A Long–Term Single–Blind Study"; Urology, vol. 51, 620–626;1998.

H. Willmann, et al; "Lecithin Organogel as Matrix for Transdermal Transport of Drugs"; Journal of Pharmaceutical Science, vol. 81, No. 9; 1992.

* cited by examiner

*Primary Examiner*—Raj Bawa
(74) *Attorney, Agent, or Firm*—David G. Henry

(57) ABSTRACT

The invention is of a topical medicament and associated methodology for use thereof, through the use of which fibrotic or connective tissue disorders involving scarring, sub-dermal plaque accumulations or fibrosis of muscle tissue may be effectively, cost effectively, and painlessly treated. One or more calcium channel blocker agents serve as the primary active ingredient of the present compositions, with carrier agents facilitating non-invasive transdermal delivery of the calcium channel blocker(s) to subdermal disease sites.

1 Claim, No Drawings

COMPOSITION AND METHOD FOR TOPICALLY TREATING PEYRONIE'S DISEASE, DUPUYTREN'S HAND CONTRACTURE, LEDDERHOSE FIBROSIS, ERECTILE DYSFUNCTION ARISING FROM PLAQUE ACCUMULATIONS, AND SCARRING

CITATION TO PRIOR APPLICATION

This is a continuation-in-part with respect to U.S. application, Ser. No. 09/128,103, filed Aug. 3, 1998 now U.S. Pat. No. 6,031,005 from which priority is claimed under 35 U.S.C. §120.

BACKGROUND OF THE INVENTION

1. Field of the Invention

Applicant's invention relates to medicaments and treatment procedures relating to connective tissue disorders manifested by sub-dermal plaque accumulations as well as to fibrosis of muscle tissues, some example of which result in total or partial erectile dysfunction. Representative examples of such sub-dermal plaque accumulation disorders include Peyronie's Disease, Ledderhose Fibrosis, Dupuytren's contracture of the hand and certain forms of erectile dysfunction.

2. Background Information

A. Peyronie's Disease

An initial focus of the present invention—Peyronie's disease—has likely plagued men for time immemorial, but has been recognized as a distinct malady for no less than 400 years. Peyronie's disease was first described in 1743 by a French surgeon, Francois de la Peyronie. The disease was written about as early as 1687 and was oftentimes associated with impotence.

As with the other plaque manifested disorders to which the present invention relates, the symptoms of Peyronie's disease and of its severity vary to some degree. The most common manifestation of Peyronie's disease is in the form of a "lump," "plaque" or "hard" area in the non-erect penis. With or without these palpable symptoms, painful erections and penile disfigurement are often associated with the malady.

The pain and disfigurement associated with Peyronie's disease relate to the physical structure of the penis in which is found two erectile rods, called the corpora cavernosa, a conduit (the urethra) through which urine flows from the bladder, and the tunica which separates the cavernosa from the outer layers of skin of the penis. A person exhibiting Peyronie's disease will have formation(s) of plaque or scar tissue between the tunica and these outer layers of the skin (referred to as "sub-dermal" in this application). The scaning or plaque accumulation of the tunica reduces its elasticity causes such that, in the affected area, it will not stretch to the same degree (if at all) as the surrounding, unaffected tissues. Thus, the erect penis bends in the direction of the scar or plaque accumulation, often with associated pain of some degree.

Peyronie's disease often occurs in a mild form and heals spontaneously in 6 to 15 months. However, in severe cases, the hardened plaque substantially reduces penile flexibility and causes excruciating pain as the penis is forced into a highly arcuate or even serpentine configuration. A plaque on the top of the shaft (most common) causes the penis to bed upward; a plaque on the underside causes it to bend downward. In some cases, the plague develops on both top and bottom, leading to indentation and shortening of the penis.

In all but minor manifestations of Peyronie's disease, the victim has some degree of sexual dysfunction. In more severe cases, sexual intercourse is either impossible, or is so painful as to be effectively prohibitive.

While plaque of Peyronie's disease is itself benign, or noncancerous, this is of little solace to sufferers of the disease.

Empirical evidence indicates an incidence of Peyronie's disease in approximately one percent of the male population. Although the disease occurs mostly in middle-aged men, younger and older men can acquire it. About 30 percent of men with Peyronie's disease also develop fibrosis (hardened cells) in other elastic tissues of the body, such as on the hand or foot. Common example of such other conditions include Dupuytren's contracture of the hand and Ledderhose Fibrosis of the foot.

Many researchers believe the plaque of Peyronie's disease develops following trauma to the penis (hitting or bending) that causes localized bleeding inside the penis. If the penis is abnormally bumped or bent, an area where the septum attaches to the elastic fibers surrounding the corpora cavernosa may stretch beyond its normal limit, injuring the lining of the erectile chamber and, for example, rupturing small blood vessels. Also, as a result of aging, diminished elasticity near the point of attachment to the septum may tend to increase the chances of injury of this nature.

Such a damaged area may heal slowly or abnormally because of repeated trauma to the same area and/or because of the natural, minimal amount of blood-flow in the sheath-like fibers of the elastic structures of the penis. In cases of Peyronie's disease which tend to heal within about a year, the plaque does not tend to advance beyond an initial inflammatory phase. In cases that persist for longer periods, the plaque typically undergoes fibrosis, or the formation of tough fibrous tissue, and even calcification, or the formation of calcium deposits.

While trauma might explain acute cases of Peyronie's disease, it does not explain why most cases develop slowly and with no apparent traumatic event. It also does not explain why some cases disappear quickly, and why similar conditions, such as Dupuytren's contracture, do not seem to result from severe trauma.

In some cases, men who are related by blood tend to develop Peyronie's disease, which suggests a possible genetic predisposition to Peyronie's disease.

B. Present Treatment of Peyronie's Disease

Because the cause(s) and development of Peyronie's disease are not well understood, physicians to this day treat the disease with a largely experimental approach—they discontinue anything which lacks apparent efficacy, and continue anything that seems to help.

Surgery is the only approach to treating Peyronie's disease which appears to have predictably repeatable efficacy. Surgery is usually only indicated in long-term cases where the disease is stabilized and the deformity prevents intercourse and/or causes extreme pain. However, complications can develop from surgery, including a permanent shortening of the penis.

Attempts at simple plaque excision were described in the 19th century by MaClellan, Regnoli and Huitfield, but by the early 20th century most authors described this technique as disastrous. For this reason Young developed a procedure that simply "freed" the plaque from the tunica albuginea in order to improve erectile dynamics. Lowsely and Boyce then re-explored the technique of simple plaque excision by adding the interposition of a "pat-pad" graft into the defect. Although many others continued to report success with this technique, it failed to gain general acceptance as the treatment of choice.

In 1995 Nesbit described the correction of congenital penile curvature with multiple elliptical excisions of the corporeal tunica. To this day, many surgeons prefer this technique for the correction of the Peyronie's bend. However, the inevitable penile shortening led Devine and Horton (1974) to experiment with further grafting procedures. Having experimented with fascial, arterial and venous patches in dogs, they came to the conclusion that dermal grafts were the least likely to "contract" and so reproduce the defect. To this day, many other grafting materials have been tried including autologous vein, temporoparietal fascia, tunica vaginalis, gortex and dacron.

The cost of the various surgical approaches to Peyronie's disease (no less than around $6,500) is, alone, often a deterrent to many Peyronie's disease sufferers in adopting this particular approach to treatment. While surgical intervention was, prior to the present invention, the most likely effective treatment in any given case of Peyronie's disease, the condition does often reappear, even after surgery.

The other, presently known, non-surgical approaches to Peyronie's disease treatment are many and varied, although they are all largely ineffective. Attempts to dissolve the plaque by direct intra-lesional injections have been tried since the late 19th century. Walsham and Spencer injected both mercury and iodide and intra-lesional injections of fibrinolysins were used in the 1820's. Teasley introduced the concept of intra-lesional steroid injections in 1954, although the pain caused by the high injection pressures led many surgeons to perform the procedure under general anaesthetic. In 1959 Hinman developed a "high pressure" screw-threaded injection device that was somewhat effective in certain cases, and could be used with no anaesthesia, but still lacked predictable efficacy. More recently, intra-lesional injections of agents such as Verapamil and clostridial collagenase have been tried, but with very limited success.

Of the injection methodologies, those involving clostridial collagenase appear to exhibit the most consistent efficacy, though still quite limited in effect and duration. Collagenase is likely effective through its ability to dissolve collagen, the major component of the plaque of Peyronie's disease.

Both external beam radiation treatment and intra-lesional implantation of radium seeds have been tried since the turn of the 20th century. In 1921, Sonntag reviewed this practice and claimed that these treatments were actively detrimental. Despite this, radiation therapy had been used in many clinics over the years and some authorities still claim that success can be anticipated if a radiation regimen is initiated early in the course of the disease. Radiation treatment is also said to be particularly effective for treating patients whose predominant symptom is pain (as opposed to severe disfigurement).

As technologies have evolved, so have the associated energy sources which have been applied to treat Peyronie's disease. Early in the 20th century, diathermy current was used to generate heat to treat the plaque and eventually low voltage electrical devices were developed and sold for use in the home. Perhaps the most imaginative variant was the technique known as histamine iontophoresis. This combined the use of electrodes with a "plaque busting" solution that was supposedly absorbed into the penis when an electrical gradient was applied. In more recent times, both ultraviolet light and local ultrasound have surfaced and submerged in the treatment history.

Not surprisingly, the inevitable application of laser technology has recently emerged as a means of "vaporizing" the plaque. Again, the efficacy of this latest treatment is open to serious question.

The staggering array of treatment options for Peyronie's disease (failed attempts, really), and the invested effort, cost and intellectual energy which they represent, are testament to the serious need that remains for an effective treatment for Peyronie's disease, and one which patients can tolerate from cost, comfort and convenience perspectives.

All-in-all, there is simply no truly effective treatment of Peyronie's disease—a disease which often produces such severe discomfort and distress that sufferers have been willing to endure such treatments as penile injections.

C. Other Fibrotic Disorders

As mentioned above, Peyronie's disease is not the only condition which manifests itself via sub-dermal plaques. Dupuytren's contracture of the hand, and Ledderhose Fibrosis are additional examples. Discussions herein concerning the treatment regimen and efficacy in the treatment of Peyronie's disease through practice of the present invention are equally applicable to such other fibrotic disorders.

The medicaments of the present invention have been used in treating both Dupuytren's contracture of the hand, and Ledderhose Fibrosis. In these instances, efficacy in treating Dupuytren's contracture of the hand, and Ledderhose Fibrosis through topical application of the present medicaments equal that of treating Peyronie's disease.

D. Erectile Dysfunction

Fibrosis is a common response to numerous conditions, including but not limited to the following:

Aging

Tissue necrosis

Trauma or Injury

Connective Tissue Disease

Hypertension

Diabetes

Arterial Insufficiency

Atherosclerosis

Fibrosis of cavemosal smooth muscle tissue results in the loss of elasticity of this smooth muscle tissue, thereby interfering with the normal expansion of the cavernosal chambers when filled with arterial blood. Therefore, a partial penile erection or no erection may occur.

Erectile dysfunction due to fibrosis is common from the fifth through the eighth decade of life, while the capacity for erection often is not changed. A hypothesis of the present inventor was that, because fibrosis underlies certain forms of erectile dysfunction, his topical, calcium channel blocker medicaments might be efficacious in treating such forms of erectile dysfunction as arise from fibrosis because of the common causative roots of fibrosis-related erectile dysfunction and Peyronie's disease—excessive formation of connective tissue.

As discussed below, the inventor's hypothesis proved correct.

E. Reduction of Existing Scars

Yet another use for compositions and methods of use of the present invention involves the remediation of existing scars. Preliminary research indicates that topical calcium channel blocker preparations of the present invention exhibit a high degree of efficacy in reducing objective manifestations of scar tissues. Compositions of the present invention have been applied in a like dosage and periodicity as described above to a variety of scar types with thus far successful results. In the limited number of cases to date, the dimensions and, when applicable, aberrant coloration of existing scars were substantially reduced and similar time frames as those observed in the use of such compositions in the treatment of the sub-dermal plaque accumulations of Peyronie's disease-like maladies. Indications, particularly from plastic surgeons, are to the effect that the treatment of existing scarring through use of the present compositions appears to provide scar remediation with an unprecedented combination of ease of treatment, lack of pain and efficacy.

SUMMARY OF THE INVENTION

It is an object of the present invention to provide a novel medicament useful in the treatment of connective tissue disorders, exemplified by sub-dermal plaque formation and accumulation, such as Peyronie's disease, Dupuytren's contracture, Ledderhose Fibrosis and fibrosis of muscle tissue such as underlies erectile dysfunction.

It is another object of the present invention to provide a novel and unobvious medicament useful in the treatment of conditions characterized by hyperprolipheration of connective tissue such as Peyronie's disease, Dupuytren's contracture, Ledderhose Fibrosis, and scarring.

It is another object of the present invention to provide a novel and unobvious medicament useful in the treatment of fibrotic tissue disorders, which medicament is more effective than existing means for treatment.

It is another object of the present invention to provide a novel and unobvious medicament useful in the treatment of connective tissue disorders through the non-invasive, topical application thereof.

It is another object of the present invention to provide a novel and unobvious medicament useful in the treatment of connective tissue disorders through the non-invasive, topical application thereof, which topical application is of at least equal efficacy than invasive and/or less convenient treatment regimens.

In satisfaction of these and related objectives, Applicant's present invention provides a topical medicament and associated methodology for use thereof, through the use of which Peyronie's disease, Dupuytren's contracture, Ledderhose Fibrosis, and related fibrotic tissues disorders (including scarring and fibrosis-based erectile dysfunction) may be effectively, cost effectively, and painlessly treated.

The invention, although exemplified by specific embodiments which are based upon, or rely on the use of specific calcium channel blockers, is not limited to such species. Rather, observations by the present inventor indicate that when coupled with a suitable carrier for transdennal delivery, all thus-far-evaluated calcium channel blockers effect reduction of fibrotic tissue disorder symptoms. Therefore, the true scope of the invention encompasses preparations and methods of use facilitating or involving the use of transdermal application of calcium channel blockers in the treatment of fibrotic tissue disorders which exhibit subdennal plaque accumulations (Peyronie's disease, Dupuytren's contracture, and Ledderhose Fibrosis, for example) or scarring.

The medicament of the present invention is a topical gel which has repeatably effected, in many cases, a complete reversal of perceptible Peyronie's disease symptoms, and in all cases, a substantial reduction of such symptoms to a substantially greater degree and substantially higher incidence than previously experienced by patient populations over-all, and in individual instances wherein patients had previously attempted alternative treatment regimens.

All observations of efficacy of the present compositions and methods arise from physician-supervised and prescribed treatment regimens involving use of the medicaments of the present invention. In most cases to date, use of the present medicaments and prescribed treatment regimens followed prior, wholly or substantially unsuccessful attempts to treat patients' fibrotic tissue disorders, most such cases to date involving Peyronie's disease. Recent studies (as discussed below) involve the treatment of erectile dysfunction though use of the medicaments taught herein. These later studies indicate that use of topical calcium channel blocker medicaments taught herein are highly effective in treating erectile dysfunction which appear to relate to fibrosis of cavernosal smooth muscle tissue.

In a experimental study, 142 patients reporting decreased quality erections were treated with topical Verapamil (80 mg/mL). One hundred thirty four (94.3%) experienced improvement of erectile rigidity and/or improvement of penile girth upon erection. These patients applied 0.5 mL of the Verapamil topical compound to the entire shaft of the penis twice a day. The length of treatment varied from one to several months, with the mean treatment period being 3.5 months. Patients were either examined or interviewed and counseled at least every thirty days in order to evaluate progress and monitor side effects. The only side effect reported was contact dermatitis in less than one percent of the patient population. This side effect was easily controlled with topical corticosteroids.

Similar results have been observed in patients treated with a topical Nifedipine compound (40–60 mg/ml) or a combination of Verapamil and Nifedipine.

Formulations for the topical Verapamil, Nifedipine, and combination Verapamil-Nifedipine are identical to those provided herein with respect to Peyronie's Disease and the other discussed connective tissue disorders.

Upon initial suggestion of the present compositions and methods for use in treating fibrotic or connective tissue disorders, the present inventor experienced, at the hands of experienced practitioners in the field, expressions of serious doubt as to efficacy, and, in some cases, outright ridicule. The stated basis for such initial doubts and criticisms related to the fact that intralessional injections of precisely the same substances (calcium channel blockers) in the attempted treatment of Peyronie's disease and similar fibrotic tissue disorders had yielded very sporadic and limited results. The present inventor was told repeatedly by those experienced in the treatment of fibrotic tissue disorders (Peyronie's disease, in particular) that a topical preparation based on calcium channel blockers could "never" have efficacy in view of the failure of injections of the same substances directly into the plaques of these conditions. As mentioned previously, actual experience teaches that the strikingly counter-intuitive effect of the compositions and methods of the present invention in the treatment of fibrotic tissue disorders is very much real—a fact born out by the substantial commercial success of the present medicaments in a very short time (less than a year at the time of preparation of this application) and with no commercial marketing whatsoever, as well as the immediate replacement of existing treatment regimens by the medicaments and methods of the present invention by numerous medical practitioners.

Another remarkable use of the medicaments of the present invention (all based on topically applied calcium channel blocker preparations) relates to the treatment of existing scars, such as arise from injury and surgical procedures. Preliminary studies indicate that the topical channel blocker preparations of the present invention, when applied to existing scars (as opposed to sites of injury in any attempt to prevent scar formation ab initio) substantially reduces the dimensions and color aberrations of scars.

DETAILED DESCRIPTION OF THE PREFERRED EMBODIMENT

A. Preparation of Calcium Channel Blocker Preparations

In the preferred embodiment, the primary active ingredient of the topical gel is a diphenylalkylamine. However, it should be understood that other calcium channel blockers (topically applied in a similar composition) provide similar relief. The presently preferred embodiment of the present medicament utilizes Verapamil Hydrochloride, USP calcium channel blocker of choice. With certain patients, combinations of channel blocker agents seem to have an even greater efficacy than a single such agent. For example, limited trials to date indicate that in certain, but not all, cases, a mixture of differing classes of calcium channel blockers. One such example includes a mixture in roughly equal proportions of a diphenylalkylamine (Verapamil Hydrochloride, USP, for example) and a dihydropyridines (Nifedipine, for example).

Other calcium channel blockers include benzothiazepines (Diltiazem, for example), other dihydropyridines (Amlodipine, Felodipine, Isradipine, Nicardipine, Nimodipine, or Nisoldipine), and the fast sodium inward channel inhibitor—Bepridil.

The preferred Verapamil-based gel of the present invention includes two constituent preparations—Lecithin Isopropyl Myristate Reagent and Pluronic F127 Gel 20%. Preparation of the presently preferred embodiment and best mode of the composition proceeds as follows (with alterations as attend larger scale production, such as by pharmaceutical companies, being within the scope of the invention):

Ingredients

Verapamil Hcl, USP, NDC 51552-525-50 CAS 152-114

Ethoxy Diglycol Reagent CAS 111-90-0

Poloxamer, NF (407)(Pluronic F127) NDC 38779-0834-8 CAS 9003-11-6

Lecithin, NF 18 (Granular) NDC 38779-0947-3 CAS 80020-43-5

Isopropyl Myristate, NF CAS 110-27-0

Sterile Water for Irrigation NDC 0074-7139-09

Potassium Sorbate, NF NDC 38779-0833-5 CAS 590-00-1

Sorbic Acid, NP-FCC Powder CAS 110-44-1

Note: NDC and CAS identification numbers vary with manufacturers/suppliers. The numbers shown above are representative examples only.

| Preparation of Lecithin Isopropyl Myristate Reagent, 1,100 mL: | | |
|---|---|---|
| 1. | Lecithin, NF | 500 Gm |
| 2. | Isopropyl Myristate, NF (Cosmetic Grade) | 532 mL |
| 3. | Sorbic Acid, NF-FCC Powder | 2.7 Gm |

Place Lecithin and Sorbic Acid in a glass beaker sufficient to hold 1,100 ml of liquid. Pour Isopropyl Myristate over Lecithin and Sorbic Acid to disperse therein. Cover and allow to sit at room temperature until a smooth syrupy liquid is formed. Stir well and transfer to an amber, light-resistant glass container.

| Prepare Poloxamer (407) (Pluronic F127) Reagent, 20%, 800 mL: | | |
|---|---|---|
| 1. | Poloxamer (407) (Pluronic F127) | 160 Gm |
| 2. | Potassium Sorbate, NF | 2.4 Gm |
| 3. | Sterile Water for Irrigation qs | 800 mL |

Place the Poloxamer (407)(Pluronic F127) and the Potassium Sorbate in a 1000 mL glass beaker. Pour the Sterile Water for Irrigation over these reagents sufficient to show 800 mL on the beaker container. Stir sufficiently to wet the dry reagents with the water. Place in a scientific grade, digital temperature-controlled refrigerator atmospherically controlled between 39 and 42 degrees Centigrade. Allow to stand until all reagents have dissolved in the water. Add additional sterile water for irrigation sufficient to yield 800 ml. Stir well and transfer to a clean glass or plastic container. This reagent must be stored in the refrigerator at the above designated temperature range.

Preparation of Topical Verapamil 80 mg/mL Final Product

1. Weigh 4.8 GM Verapamil HCl, USP and place in a 100 mL glass beaker.
2. Add 7 mL Ethoxy Diglycol Reagent to Verapamil and stir well.
3. Place Verapamil/Ethoxy Diglycol Reagent mixture on a laboratory grade hot plate that has been pre-heated between 60–80 degrees Centigrade. Stir periodically until all Verapamil is dissolved and a clear solution exists.
4. Remove Verapamil solution from hot plate and add 16 mL of the pre-prepared Lecithin Isopropyl Myristate reagent and stir well. Using a 16 G needle luer-locked to a 60 cc syringe, transfer the Verapamil/Lecithin Isopropyl Myristate suspension from the beaker to the 60 cc syringe.
5. Remove the Poloxamer (407) (Pluronic F127) Reagent, 20% from the refrigerator and draw up 34 mL into a second 60 cc luer-lock syringe.
6. Using a Luer Lock To Luer Lock Adapter (Baxa 13901), attach the two 60 cc syringes containing the reagents (one syringe to each side of the Adapter) in preparation for mixing the two together.
7. With adequate pressure applied to the plunger of each 60 cc syringe, force the materials from one syringe to the other, back and forth, at least 25 times, until a smooth, consistent, and creamy mixture is prepared. Discard the empty 60 cc syringe. The final mixture should be pH 5.8–6.2 (pH 6.0 is ideal). Phosphate buffer solution may be used to adjust the pH of this product.
8. Remove the Luer Lock To Luer Lock Adapter from the 60 cc syringe containing the Verapamil mixture and cap the syringe. Protect from light by placing in an amber zip-lock bag for storage.
9. Dispense in 0.5 or 1.0 mL amber-colored plastic containers fitted with an adequate cap for patient use. Place containers in a brown zip-lock bag for further light protection. An example is a 1.0 mL amber syringe (Baxa Oral-Topical Exacta-Med Dispenser) with blue self-uprighting plastic cap. A Baxa Luer Lock-to-Oral Slip #42703 Adapter may be used to transfer the Verapamil compound from the 60 cc syringe to the 1.0 cc Baxa Exacta-Med Dispensers.
10. Label (or, as appropriate, provide patient information sheets containing the following information)

Topical Administration of Verapamil40 mg/0.5 ml for Peyronie's Disease

Do Not Refrigerate

Protect From Light

For External Use Only

This medication must not be refrigerated. Refrigeration may destroy the absorption qualities of the carrier agent(s).

Important: Do not take supplemental Vitamin C while using this medication. It may counteract the results.

Avoid tea and purple-skinned fruit since they may contain chemicals called anthocyanins that interfere with the desired action of the drug.

Take at least 500 mg Calcium twice a day with food and an 8 oz glass of water. Calcium citrate may settle better on the stomach.

Take 50 mg Zinc once a day with food.

Preparation of other calcium channel blocker-based topical medicaments useful in treating connective tissue disorders is insubstantially different (if at all), from the preparation of the above-described Verapamil-based gel. Step-by-step procedures for every variation and combination of calcium channel blockers in a topical medicament which itself, and its method of use, would be within the scope of the present invention is both unnecessary to provide an enabling disclosure and is unnecessary from a practical standpoint. The presently preferred embodiment of a calcium channel blocker-based medicament according to the present invention is as described above with respect to Verapamil. Furthermore, any compounding pharmacist of typical skill can, once exposed to the information taught herein, readily prepare calcium channel blocker-based medicaments for use in practicing the present invention, regardless of the specific identities of the prescribed calcium channel blocker(s). Nevertheless, a benzothiazepine-based medicament, using Diltiazem as the active ingredient, is prepared described below.

Preparation of Diltiazem 100 mg/ml Topical Yield is 60 mL

1. Weigh 6.0 grams of Diltiazem powder in a glass beaker. Add 5.0 mL of sterile water for irrigation and stir well. Place on a laboratory hot plate preheated between 50–70 degrees centigrade and stir until Diltiazem is dissolved and a clear solution exists.
2. Add 2.0 mL propylene glycol and stir well.
3. Add 2.5 ml 5-Ethyl-2,8-diisopropyl-1-aza-3,7-dioxabicyclo[3.3.0]octane and stir well.
4. Draw solution into a 60 mL sterile syringe using a 16 G-1" needle. Remove needle.
5. Draw 16 mL Lecithin Isopropyl Myristate Reagent into a 30 mL sterile syringe and add to the 60 mL syringe containing the Diltiazem solution using a 16 G-1" needle to make the transfer.
6. Mix the ingredients in the 60 mL syringe well by gentle inversion.
7. Draw 30 mL of 20% Pluronic F-127 Organogel into a second 60 mL sterile syringe.
8. Using a luer lock to luer lock adapter, connect the two 60 mL syringes containing reagents.
9. By pushing the ingredients back and forth between the two 60 mL syringes, using force, perform this operation until a clear consistent gel exists. This usually requires 50–60 transfers from one syringe to the other.
10. Dispense in 3 mL amber oral syringes and store at room temperature.

B. Use of Medicaments in Treating Peyronie's Disease

Calcium channel blocker medicaments prepared and to be used according to the present invention are, according to the preferred mode of use, dispensed in one-ml amber syringes that are graduated in 0.01 ml increments with major graduations at 0.1 through 1.0 ml. Each syringe is filled to the 1.0 ml mark. One dose (40 mg) of Verapamil-based gel is contained in 0.5 ml. Each syringe is capped with a tip that can be removed and replaced by simply pushing and pulling with a twist.

The patient is to apply 0.5 ml (40 mg) twice a day, in the morning and after a shower in the evening. The old dose must be completely removed and the area cleaned and dried before a new dose is applied. One syringe will last one (1) day.

The patient removes the cap and dispels 0.5 ml by pushing the plunger to the 0.5 ml mark (the first dose). The $2^{nd}$ dose will empty the syringe. One syringe, therefore, will last one day. The patient should apply the medication by starting at the point where the plaque is heaviest or where the curvature begins and work out until the entire penile shaft has been covered with medication.

Patients should not engage in intercourse with the medication applied as it may irritate the vaginal mucosa.

The patient's progress should be evaluated every 4 weeks to assess changes in plaque, etc. Although some patients respond to the medication during the first month of therapy, others have responded after 2–3 months of therapy. It is important to not miss doses of medication.

Application to the entire penile shaft is important. In initial experimental use of the present medicament, localized application of the gel (solely to areas atop the suspected plaque) effected merely a change in the direction of the previous curvature. Subsequent application to the entire penile shaft in the same patients resulted in complete reversal of symptoms. This phenomena may be explained if plaque, to varying degrees, is present throughout the entire penile shaft, and not just localized to the point(s) of curvature.

During the treatment regimen, each patient's progress should be evaluated, at least every two weeks. If no results have occurred by the end of the 3rd week, the dose should be increased and/or the medicament applied more often than twice daily.

Since calcium channel blockers may be antihypertensive, the patient's blood pressure should be monitored at the physician's office after the first dose of a calcium channel blocker medicament is applied. To date, however, no changes in blood pressure have been noted.

C. Likely Mechanism of Action and Examples of Efficacy

It should be noted that Verapamil, a calcium channel blocker, is commonly given orally or intravenously to treat cardiac arrhythmias and/or hypertension. Verapamil is even one of the substances which has been injected directly into the plaque of Peyronie's disease sufferers. However, despite the pain and psychological distress associated with penile injections of any kind, it has not heretofore occurred to anyone to compound a topical Verapamil preparation for use in treating Peyronie's disease or other maladies which exhibit sub-dermal plaque accumulations (Dupuytren's contracture, and Ledderhose Fibrosis, for example). It appears that the very limited success of direct application of Verapamil to plaques through injection would have logically deterred practitioners from applying the same substance in a less direct manner—through topical application.

The mechanism of action of the topical calcium channel blocker-based medicaments and methods of treatment are, as yet, unclear to the present inventor and to the clinicians who have thus far used and evaluated the same. The present inventor believes, however, that, upon absorption of the drug through the skin into the plaque, the calcium channel blocking properties of Verapamil (and other calcium channel blocking agents) causes the body to produce collagenase.

Collagenase, in turn, dissolves the collagen of which the plaque is primarily formed.

The present belief of the inventor is that the collagen that comprises the majority of the plaque or scar tissue of fibrotic tissue disorders contain peptides I, II and III substrates of fibroblast collagenase. When applied transdermally, a calcium channel blocker is absorbed uniformly into the fibrotic tissue (plaque) and prevents divalent calcium ions from entering the cell membranes. The calcium ions that are blocked, as well as zinc ions, bind with the peptides I, II and III substrates of fibroblast collagenase, thereby forming a ternary complex which triggers the completion of the formation of the collagenase that is highly specific for the subject collagen. This collagenase is produced in sufficient quantities to catabolize the collagen. The collagen can be type I, II or III, and the collagenase produced would specifically match each respective type.

The lack of efficacy experienced through the use of injected calcium channel blocker preparations in the treatment of fibrotic tissue disorders involving sub-dermal plaque accumulations appears to arise from the inability of an injected quantum of calcium channel blocker to be adequately disbursed through the one or more plaque accumulations to effect significant remediation of the patient's overall condition.

Whatever the mechanism, the present medicament shows an astonishing efficacy, particularly considering the miserable failure of such closely related prior attempts at Peyronie's disease treatment. One patient involved in experimental evaluation of the present medicament exhibited a penile curvature in excess of 75 degrees—a condition which was both painful and which effectively rendered the individual completely sexually dysfunctional. After using the medicament of the present invention, in the prescribed manner, this patient's Peyronie's disease symptoms were completely reversed in two week's time. Other experimental patients, albeit with less severe symptoms, have shown equally remarkable and complete recoveries, including one patient who suffered from Peyronie's disease for over sixty years, never having previously experienced success with any prior treatment regimen undertaken by numerous physicians..

While the initial dose of the preferred Verapamil gel has, to date, been 0.50 ml (containing 40 mg of Verapamil) applied twice daily, in the morning and at night, it is suspected that, once a patient receives relief, the plaque may re-form if the medication is stopped. In that event, continued use of the present medicament, perhaps at a lower dose, or less frequently, may be indicated.

D. Other Fibrotic Disorders

The medicaments of the present invention have been used in treating both Dupuytren's contracture of the hand, and Ledderhose Fibrosis. In these instances, efficacy in treating Dupuytren's contracture of the hand, and Ledderhose Fibrosis through simple topical application of the present medicaments equal that of treating Peyronie's disease.

E. Erectile Dysfunction

The use of the present medicaments in the treatment of fibrosis-related erectile dysfunction is, according to experience to date, identical to the use in treating Peyronie's disease. Variations of dosage and periodicity of treatments may be indicated by further research, but the present experiments using identical treatment regimens to those described above for Peyronie's diseases have yielded a very high rate of positive results.

F. Treatment of Existing Scars

Yet another use for compositions and methods of use of the present invention involves the remediation of existing scars. Preliminary research indicates that topical calcium channel blocker preparations of the present invention exhibit a high degree of efficacy in reducing objective manifestations of scar tissues. Compositions of the present invention have been applied in a like dosage and periodicity as described above to a variety of scar types with thus far successful results. In the limited number of cases to date, the dimensions and, when applicable, aberrant coloration of existing scars were substantially reduced and similar time frames as those observed in the use of such compositions in the treatment of the sub-dermal plaque accumulations of Peyronie's disease-like maladies. Indications, particularly from plastic surgeons, are to the effect that the treatment of existing scarring through use of the present compositions (simple, topical application of the present medicaments to cover the scar with a thin film of the medicament) appears to provide scar remediation with an unprecedented combination of ease of treatment, lack of pain and efficacy.

Although the invention has been described with reference to specific embodiments, particularly with respect to the particular active ingredient of the present medicament, this description is not meant to be construed in a limited sense, in particular to limit the scope of the appended claims to cover only those medicaments and associated modalities of treatment which include Verapamil as the calcium channel blocker, the function of which in the area of plaque appears to lie at the heart of the efficacy of the present medicament. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A method for treating a connective tissue disorder selected from the group consisting of Peyronie's disease, Dupuytren's hand contracture and Ledederhose Fibrosis, each disorder manifesting sub-dermal plaque accumulations or scar tissue, wherein the method consists of non-invasive transdermal application of a topical gel composition to a portion of dermis which overlies the sub-dermal plaque or scar tissue, said composition consisting essentially of (i) a calcium channel blocker selected from the group consisting of verapamil, nifedipine, diltiazem, amalodipine, felodipine, isradipine, nicardipine, nimodipine, nisoldipine, bepridil and mixtures thereof; and (ii) a non-invasive transdermal carrier agent.

* * * * *

UNITED STATES PATENT AND TRADEMARK OFFICE

CERTIFICATE OF CORRECTION

PATENT NO. : 6,353,028 B2
APPLICATION NO. : 09/411175
DATED : March 5, 2002
INVENTOR(S) : W. Jerry Easterling It is certified that error appears in the above-identified patent and that said Letters Patent is hereby corrected as shown below:

In title page, item (54) Title, and column 1, lines 1-7, delete "COMPOSITION AND METHOD FOR TOPICALLY TREATING PEYRONIE'S DISEASE, DUPUYTREN'S HAND CONTRACTURE, LEDDERHOSE FIBROSIS, ERECTILE DYSFUNCTION ARISING FROM PLAQUE ACCUMULATIONS, AND SCARRING" and insert --METHOD FOR NON-INVASIVE TOPICAL TREATMENT OF PEYRONIE'S DISEASE, DUPUYTREN'S HAND CONTRACTURE AND LEDDERHOSE FIBROSIS-- therefor.

Signed and Sealed this

Thirteenth Day of July, 2010

David J. Kappos
*Director of the United States Patent and Trademark Office*